(12) United States Patent
Jinbo et al.

(10) Patent No.: US 10,821,119 B2
(45) Date of Patent: Nov. 3, 2020

(54) ROCURONIUM PREPARATION CAUSING LESS PAIN, METHOD FOR PRODUCING THE SAME, AND METHOD FOR REDUCING AND/OR ALLEVIATING VASCULAR PAIN TO BE INDUCED USING THE SAME

(71) Applicant: MARUISHI PHARMACEUTICAL CO., LTD., Osaka (JP)

(72) Inventors: Keisuke Jinbo, Osaka (JP); Yutaka Itsuji, Osaka (JP)

(73) Assignee: MARUISHI PHARMACEUTICAL CO., LTD., Osaka (JP)

( * ) Notice: Subject to any disclaimer, the term of this patent is extended or adjusted under 35 U.S.C. 154(b) by 140 days.

(21) Appl. No.: 14/898,259

(22) PCT Filed: Jun. 23, 2014

(86) PCT No.: PCT/JP2014/066504
§ 371 (c)(1),
(2) Date: Dec. 14, 2015

(87) PCT Pub. No.: WO2015/001995
PCT Pub. Date: Jan. 8, 2015

(65) Prior Publication Data
US 2016/0143919 A1 May 26, 2016

(30) Foreign Application Priority Data

Jul. 1, 2013 (JP) .................... 2013-138218

(51) Int. Cl.
| | |
|---|---|
| *A61K 31/58* | (2006.01) |
| *A61K 9/00* | (2006.01) |
| *A61K 47/18* | (2017.01) |
| *A61K 47/12* | (2006.01) |
| *A61K 47/24* | (2006.01) |
| *A61K 47/02* | (2006.01) |

(52) U.S. Cl.
CPC ............ *A61K 31/58* (2013.01); *A61K 9/0019* (2013.01); *A61K 47/02* (2013.01); *A61K 47/12* (2013.01); *A61K 47/18* (2013.01); *A61K 47/24* (2013.01)

(58) Field of Classification Search
CPC .................................................. A61K 31/58
USPC ........................................................ 514/176
See application file for complete search history.

(56) References Cited

U.S. PATENT DOCUMENTS

| | | | | |
|---|---|---|---|---|
| 5,418,226 A | * | 5/1995 | Sleigh .................... | C07J 43/003 514/176 |
| 6,030,941 A | * | 2/2000 | Summerton ......... | A61K 47/645 514/1.2 |
| 6,911,455 B2 | | 6/2005 | Floyd et al. | |
| 2009/0156562 A1 | | 6/2009 | Winch | |

| | | | |
|---|---|---|---|
| 2009/0182043 A1 | | 7/2009 | Nishida et al. |
| 2013/0313261 A1 | | 11/2013 | Tani et al. |
| 2016/0101231 A1 | | 4/2016 | Tani et al. |

FOREIGN PATENT DOCUMENTS

| | | |
|---|---|---|
| JP | 7-53751 | 6/1995 |
| JP | 2009-515895 | 4/2009 |
| RU | 2 329 799 | 7/2008 |
| WO | 99/27914 | 6/1999 |
| WO | 2007/059019 | 5/2007 |
| WO | 2008/065142 | 6/2008 |
| WO | 2012/073891 | 6/2012 |

OTHER PUBLICATIONS

Office Action issued in corresponding Saudi Arabian Application No. 515370275, with partial English translation.
Extended European Search Report dated Feb. 17, 2017 in corresponding European Application No. 14820424.1.
International Preliminary Report on Patentability dated Jan. 7, 2016 in International (PCT) Application No. PCT/JP2014/066504.
International Search Report dated Sep. 9, 2014 in International (PCT) Application No. PCT/JP2014/066504.
Nema et al., "Excipients and Their Use in Injectable Products", PDA Journal of Pharmaceutical Science & Technology, vol. 51, 1997, pp. 166-167.
Borgeat et al., "Spontaneous movements associated with rocuronium: is pain on injection the cause?", British Journal of Anaesthesia, vol. 79, 1997, pp. 382-383.
Pharmaceutical Interview Form ESLAX 25 mg/2.5 mL, 50 mg/5.0 mL, Revised in Jun. 2014 (rev. ver. 7), partial English translation.
Klement et al., "Pain on I.V. injection of some anaesthetic agents is evoked by the unphysiological osmolality or pH of their formulations", British Journal of Clinical Anaesthesia, vol. 66, 1991, pp. 189-195.
Woo Han et al., "Neutralized rocuronium (pH 7.4) before administration prevents injection pain in awake patients: a randomized prospective trial", Journal of Anesthesia, vol. 19, 2007, pp. 418-423.
Kawasaki et al., "Influence of infusion solution on the vascular permeability in rat skin", Folia Pharmacol. Japan, vol. 111, 1998, pp. 317-325, with English abstract.
The Japanese Journal of Surgical Metabolism and Nutrition, vol. 32, 1998, pp. 303-308, partial English translation.
Office Action dated Oct. 1, 2018 in corresponding Russian Application No. 2016102844, with English translation.

(Continued)

*Primary Examiner* — Jennifer M Kim
(74) *Attorney, Agent, or Firm* — Wenderoth, Lind & Ponack, L.L.P.

(57) ABSTRACT

Provided is a rocuronium preparation designed to reduce vascular pain to be induced. The rocuronium preparation contains rocuronium and a buffer solution, and has titratable acidity of 100 mEg or less. The buffer solution may be an acetate buffer solution, a citrate buffer solution, a formate buffer solution, a tartrate buffer solution, a phosphate buffer solution, a glycine-hydrochloric acid buffer solution, or a citric acid-phosphate buffer solution.

10 Claims, 1 Drawing Sheet

(56) References Cited

OTHER PUBLICATIONS

Decision to Grant dated Jan. 15, 2019 in corresponding Russian Patent Application No. 2016102844 with English translation.

* cited by examiner

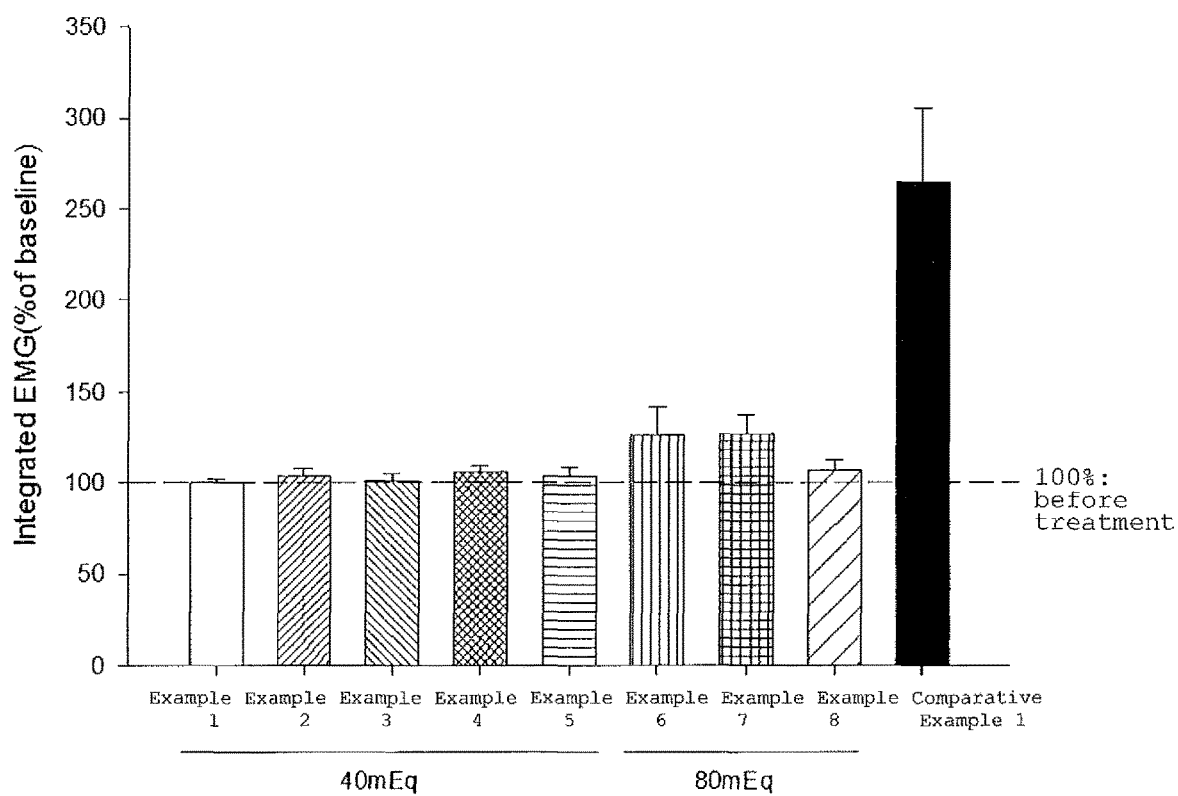
Data are represented as mean ± S.E. (n=9-10)

ROCURONIUM PREPARATION CAUSING LESS PAIN, METHOD FOR PRODUCING THE SAME, AND METHOD FOR REDUCING AND/OR ALLEVIATING VASCULAR PAIN TO BE INDUCED USING THE SAME

TECHNICAL FIELD

The present invention relates to a rocuronium preparation causing less pain, a method for producing the same, and a method for reducing and/or alleviating vascular pain to be induced using the same.

BACKGROUND ART

Rocuronium (Patent Literature 1) in the form of rocuronium bromide represented by the following formula is known as an active ingredient of an anesthetic muscle relaxant (Non Patent Literature 1).

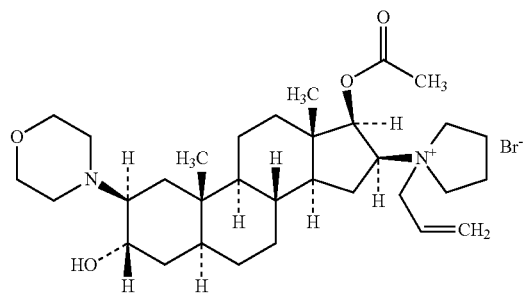

However, it was often the case that an unconscious patient to whom a known rocuronium preparation was administered exhibited sudden, forceful flexion of the wrist or the arm, or withdrawal of the hand although the unconscious patient did not complain of the pain.

It was considered that such a vascular pain was attributable to the pH of the rocuronium preparation and could be controlled by adjusting the pH (Non Patent Literature 2 and 3).

CITATION LIST

Patent Literature

Patent Literature 1: JP 07-53751 B

Non Patent Literature

Non Patent Literature 1: Drug interview form of ESLAX Intravenous 25 mg/2.5 mL and ESLAX Intravenous 50 mg/5.0 mL, revised in October, 2010
Non Patent Literature 2: British Journal of Clinical Anesthesia 1991; 66, 189-195
Non Patent Literature 3: Journal of Clinical Anesthesia (2007) 19, 418-423

SUMMARY OF INVENTION

Technical Problem

An objective of the present invention is to provide a rocuronium preparation designed to reduce the vascular pain, a method for producing the same, and a method for reducing and/or alleviating vascular pain using the same.

Solution to Problem

To achieve the above objective, the present inventors conducted intensive investigations and found that the vascular pain caused by a rocuronium preparation, which pain was previously attributed to the pH, can be reduced by limiting the titratable acidity of the buffer solution contained in the rocuronium preparation to 100 mEq or less. Based on this finding, the present inventors conducted further research and completed the present invention.

That is, the present invention relates to the following.

(1) A rocuronium preparation containing rocuronium and a buffer solution and having a titratable acidity of 100 mEq or less.

(2) The rocuronium preparation of the above (1) having a pH of 6 or less.

(3) The rocuronium preparation of the above (1) or (2) having a titratable acidity of 80 mEq or less.

(4) The rocuronium preparation of any one of the above (1) to (3) having a pH of 2.5 to 4.5.

(5) The rocuronium preparation of any one of the above (1) to (4), wherein the buffer solution is one or more kinds selected from an acetate buffer solution, a citrate buffer solution, a formate buffer solution, a tartrate buffer solution, a phosphate buffer solution, a glycine-hydrochloric acid buffer solution, and a citric acid-phosphate buffer solution.

(6) The rocuronium preparation of any one of the above (1) to (5), which is an injection.

(7) A method for producing the rocuronium preparation of any one of the above (1) to (6), the method comprising a step of adjusting the titratable acidity of the rocuronium preparation containing rocuronium and a buffer solution to 100 mEq or less.

(8) The method for producing the rocuronium preparation of the above (7), the method comprising a step of adjusting the titratable acidity to 100 mEq or less and the pH to 6 or less.

(9) A method for reducing and/or alleviating the vascular pain caused by a rocuronium preparation, the method comprising adjusting the titratable acidity of a rocuronium preparation containing rocuronium and a buffer solution to 100 mEq or less.

Advantageous Effects of Invention

The rocuronium preparation of the present invention is designed to reduce vascular pain to be induced.

BRIEF DESCRIPTION OF DRAWINGS

FIG. 1 shows the results of Test Example 1.

DESCRIPTION OF EMBODIMENTS

The rocuronium preparation of the present invention contains rocuronium and a buffer solution and has a titratable acidity of 100 mEq or less.

The rocuronium as an active ingredient of the rocuronium preparation used in the present invention is rocuronium bromide (chemical name: (+)-(17β-acetoxy-3α-hydroxy-2β-morpholino-5α-androstan-16β-yl)-1-allyl-1-pyrrolidinium bromide) represented by the following formula.

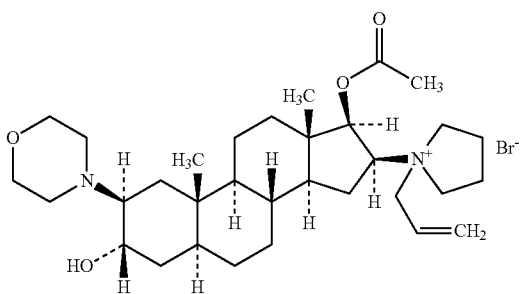

The amount of the rocuronium used in the rocuronium preparation of the present invention is not particularly limited and appropriately selected depending on the disease condition, the dosage form, etc., but is usually about 0.1 to 10% by mass, preferably about 0.5 to 5% by mass, and more preferably about 0.8 to 3% by mass relative to the total mass of the medical preparation. The dosage amount varies with the age, the sex, and the weight of the patient, the severity of the disease, etc., and therefore is not particularly limited, but generally, the daily total dose of the active ingredient is usually about 0.01 to 100 mg, and preferably about 10 to 60 mg per adult. Also, the dosage and administration method vary with the age, the sex, and the weight of the patient, the severity of the disease, etc., and therefore is not particularly limited, but generally, it is appropriate that the daily total dose is administered once daily or administered as multiple (for example 2 to 4) divided doses. In an exemplary method, the rocuronium bromide is intravenously administered in a dose of 0.6 mg/kg, and as needed, additionally administered by continuous infusion in a dose of 0.1 to 0.2 mg/kg during the operation.

The dosage form of the rocuronium preparation of the present invention is not particularly limited, but usually a solution. Examples of the solution include parenteral preparations, such as injections (for intravenous injection, intraarterial injection, intramuscular injection, subcutaneous injection, intradermal injection, intraperitoneal injection, intraspinal injection, or epidural injection), ophthalmic preparations, and intranasal preparations. The administration route of the rocuronium preparation of the present invention is not particularly limited, but in the cases of parenteral administration using injections, it is preferable to appropriately select the route from preferred routes including intravenous, intraarterial, subcutaneous, intradermal, intramuscular, and intraperitoneal administration routes depending on the age of the patient, the disease condition, and/or other conditions.

The pH of the rocuronium preparation of the present invention is not particularly limited, but considering the stability of the rocuronium, pH 6.0 or less is preferred, pH 2.5 to 4.5 is more preferred, and pH 3.0 to 4.3 is still more preferred. The pH may be a value at a temperature of 20 to 30° C.

The buffer solution used in the present invention is not particularly limited, and examples thereof include acetate buffer solution, citrate buffer solution, formate buffer solution, tartrate buffer solution, phosphate buffer solution, glycine-hydrochloric acid buffer solution, and citric acid-phosphate buffer solution. These buffer solutions may be used alone or as a mixture of two or more kinds thereof. These buffer solutions may be commercially available products.

The titratable acidity of the rocuronium preparation of the present invention is 100 mEq or less, and for a higher reduction of vascular pain, is preferably 80 mEq or less, and more preferably 60 mEq or less. The titratable acidity of the present invention means the quantity (mEq) of sodium hydroxide consumed in titration of 1 L of a solution to pH 7.4. The titratable acidity can be adjusted by changing the type and concentration of the buffer solution used. The titratable acidity may be a value at a temperature of 20 to 30° C.

The concentration of the buffer solution is not particularly limited as long as it is within a range to allow the titratable acidity to be within the above-mentioned range. For example, in cases where the buffer solution is a citrate buffer solution (pH 4.0), the concentration may be 0.07 M or less. For example, in cases where the buffer solution is a citric acid-phosphate buffer solution (pH 4.0), the concentration may be 0.04 M or less.

The rocuronium preparation of the present invention is preferably used under anesthesia although it is not a necessary condition. The anesthetic is not particularly limited, and preferred examples thereof include an inhalation anesthetic and an intravenous anesthetic. The inhalation anesthetic is not particularly limited, and examples thereof include volatile inhalation anesthetics, such as halothane, isoflurane, enflurane, methoxyflurane, sevoflurane, and desflurane; and gaseous inhalation anesthetics, such as ethylene, cyclopropane, diethylether, chloroform, nitrous oxide, and xenon. The intravenous anesthetic is not particularly limited, and examples thereof include propofol, midazolam, ketamine, tiletamine, thiopental, methohexital, and etomidate. Preferred are propofol, midazolam, etc. These anesthetics may be used alone or as a mixture of two or more kinds thereof. These anesthetics may be commercially available products.

In the rocuronium preparation of the present invention, a carrier for drug formulation is preferably blended as needed. Examples of the carrier include a solvent, a solubilizing agent, a suspending agent, an isotonizing agent, and a soothing agent. In addition, any known additives and pharmaceutically acceptable additives usually used in the pharmaceutical field, for example, a preservative, an antioxidative agent, a stabilizing agent, and an antioxidant, may be used as needed. These additives may be used alone or as a mixture of two or more thereof as appropriate for the intended dosage form. These additives may be commercially available products.

The solvent is not particularly limited, and examples thereof include purified water, ethanol, propylene glycol, polyethylene glycol, macrogol, sesame oil, corn oil, olive oil, etc. The solubilizing agent is not particularly limited, and examples thereof include propylene glycol, D-mannitol, benzyl benzoate, ethanol, triethanolamine, sodium carbonate, sodium citrate, etc. The suspending agent is not particularly limited, and examples thereof include benzalkonium chloride, carmellose, hydroxypropylcellulose, propylene glycol, polyvinyl pyrrolidone, methyl cellulose, glycerol monostearate, sodium lauryl sulfate, lecithin, polyvinyl alcohol, etc. The isotonizing agent is not particularly limited, and examples thereof include glucose, D-sorbitol, sodium chloride, D-mannitol, glycerol, etc. The soothing agent is not particularly limited, and examples thereof include benzyl alcohol etc.

The preservative is not particularly limited, and examples thereof include ethyl p-hydroxybenzoate, chlorobutanol, benzyl alcohol, sodium dehydroacetate, sorbic acid, etc. The antioxidant is not particularly limited, and examples thereof include sodium sulfite, ascorbic acid, etc. The stabilizing agent is not particularly limited, and examples thereof include casein, sodium caseinate, etc. Examples of the antioxidant include t-butylhydroquinone, butylhydroxyanisole, butylhydroxytoluene, α-tocopherol, and derivatives thereof.

The osmotic pressure of the rocuronium preparation of the present invention is not particularly limited as long as it does not contribute to the development of vascular pain and may be 250 to 1000 mosmol/kg or 260 to 600 mosmol/kg.

The method for producing the rocuronium preparation of the present invention comprises a step of adjusting the titratable acidity of the rocuronium preparation containing rocuronium and a buffer solution to 100 mEq or less. The rocuronium and the buffer solution are as described above.

It is further preferable that, in the production method, the titratable acidity is 100 mEq or less and the pH is 6 or less. The pH is as described above.

Another embodiment of the present invention is a method for reducing and/or alleviating the vascular pain caused by a rocuronium preparation, the method comprising adjusting the titratable acidity of a rocuronium preparation containing rocuronium and a buffer solution to 100 mEq or less. The rocuronium and the buffer solution are as described above.

The present invention encompasses embodiments in which various structures described above are combined within the technical scope of the present invention in such a manner that the effect of the present invention is exerted.

EXAMPLES

Hereinafter, the present invention will be illustrated in more detail by Examples, but it is not limited thereto. Various modifications can be made within the technical idea of the present invention by those with ordinary skill in the art.

Example 1

To 100 mL of a 0.018 M citric acid aqueous solution, 61.5 mL of a 0.018 M sodium citrate aqueous solution was added to give a citrate buffer solution (I) having an adjust pH of 4. To 30 mL of the solution (I), 72 mg of an isotonizing agent (NaCl) and 1.0 g of rocuronium were added, and then the pH was adjusted to 4 by adding a pH adjuster (0.018 M citric acid aqueous solution). To this, the solution (I) was added to adjust the total volume to 100 mL. The titratable acidity of the obtained preparation was measured, and the result is shown in Table 1.

Example 2

To 100 mL of a 0.014 M citric acid aqueous solution, 0.59 g of disodium hydrogen phosphate was added to give a citric acid-phosphate buffer solution (II) having an adjust pH of 4. To 20 mL of the solution (II), 71 mg of an isotonizing agent (NaCl) and 1.0 g of rocuronium were added, and then the pH was adjusted to 4 by adding a pH adjuster (0.014 M citric acid aqueous solution). To this, the solution (II) was added to adjust the total volume to 100 mL. The titratable acidity of the obtained preparation was measured, and the result is shown in Table 1.

Example 3

To 100 mL of a 0.045 M hydrochloric acid aqueous solution, 1.75 g of glycine was added to give a glycine-hydrochloric acid buffer solution (III) having an adjust pH of 3. To 30 mL of the solution (III), 37 mg of an isotonizing agent (NaCl) and 1.0 g of rocuronium were added, and then the pH was adjusted to 3 by adding a pH adjuster (0.045 M hydrochloric acid aqueous solution). To this, the solution (III) was added to adjust the total volume to 100 mL. The titratable acidity of the obtained preparation was measured, and the result is shown in Table 1.

Example 4

To a 0.055 M tartaric acid aqueous solution, a 0.055 M sodium tartrate aqueous solution was added to give a tartrate buffer solution (IV) having an adjust pH of 4. To an aliquot of the solution (IV), as in Example 1, an isotonizing agent (NaCl) and rocuronium were added, and then the pH was adjusted to 4 by adding a pH adjuster (0.055 M tartaric acid aqueous solution). To this, the solution (IV) was added to the marking of the measuring flask. The titratable acidity of the obtained preparation was measured, and the result is shown in Table 1.

Example 5

To a 0.1 M formic acid aqueous solution, a 0.1 M sodium formate aqueous solution was added to give a formate buffer solution (V) having an adjust pH of 4. To an aliquot of the solution (V), as in Example 1, an isotonizing agent (NaCl) and rocuronium were added, and then the pH was adjusted to 4 by adding a pH adjuster (0.1 M formic acid aqueous solution). To this, the solution (V) was added to the marking of the measuring flask. The titratable acidity of the obtained preparation was measured, and the result is shown in Table 1.

Example 6

A rocuronium preparation was prepared in the same manner as in Example 1 except that the concentration of the citrate buffer solution and the pH adjuster was as shown in Table 1 below. The titratable acidity of the obtained preparation was measured, and the result is shown in Table 1.

Example 7

A rocuronium preparation was prepared in the same manner as in Example 2 except that the concentration of the citric acid aqueous solution and the pH adjuster was as shown in Table 1 below. The titratable acidity of the obtained preparation was measured, and the result is shown in Table 1.

Example 8

A rocuronium preparation was prepared in the same manner as in Example 3 except that the concentration of the hydrochloric acid aqueous solution and the pH adjuster was as shown in Table 1 below. The titratable acidity of the obtained preparation was measured, and the result is shown in Table 1.

The preparations of the above Examples 1 to 8 can be prepared by an alternative procedure. That is, rocuronium is dissolved in the acidic aqueous solution having the predetermined concentration, and the basic aqueous solution is added, with monitoring of the pH using a pH meter, to reach the predetermined pH. To this, the buffer solution having the predetermined concentration is added to the marking of the measuring flask to give the final preparation.

Comparative Example 1

A commercial rocuronium preparation (trade name: ESLAX (registered trademark) Intravenous 50 mg/5.0 mL, an acetate buffer solution, pH 4.0) was used as Comparative Example 1.

Test Example 1

Urethane was intraperitoneally injected to rats (male SD rats, 8 to 9 weeks old, 9 to 10 animals in each group) at a dose of 1.4 g/kg, and tracheal intubation was carried out. Hair around the treated area was shaved, and the skin was incised to expose blood vessels near the femoral artery. A PFA tube having a tip tapered beforehand was introduced about 2 cm into the caudal superficial epigastric artery in a retrograde manner to the site from which the femoral artery arises. A coaxial needle electrode (26 G) was inserted into the left posterior semitendinosus muscle. After the operation, the rats were kept at about 37° C. Before the start of administration, the baseline value was measured for 30 seconds. Each test solution (Examples 1 to 8 and Comparative Example 1) in an amount of 50 μL was administered through the PFA tube at a rate of 0.8 mL/sec, and electromyography (EMG) measurement was performed over 30 seconds from the start of the administration. Each test solution was repeatedly administered at intervals of 1 hour or longer. About 1 hour after the operation, 1% propofol "Maruishi" (Japanese product name) was administered to the rats, and only such individuals as to exhibit muscle contraction were used in the test. The analysis of the obtained electromyogram was performed using PowerLab (16sp, ADInstruments). The raw signals were rectified and integrated over each time period of 500 μs to give quantified data ($\mu V \cdot s^2$). The results are shown as percentage values relative to the pretreatment value (baseline=100%). The results are shown in Table 1 and FIG. 1 below.

In FIG. 1, each value is the mean±standard error.

TABLE 1

| Sample No. | pH | Concentration (M) | Titratable acidity (mEq) | Integrated EMG value (% of baseline) | SE |
|---|---|---|---|---|---|
| Example 1 | 4.0 | 0.018 | 41 | 99.97 | 2.14 |
| Example 2 | 4.0 | 0.014 (citric acid) | 43 | 103.81 | 3.87 |
| Example 3 | 3.0 | 0.045 (hydrochloric acid) | 40 | 100.94 | 4.32 |
| Example 4 | 4.0 | 0.055 | 39 | 105.51 | 3.94 |
| Example 5 | 4.0 | 0.1 | 39 | 103.38 | 5.38 |
| Example 6 | 4.0 | 0.042 | 83 | 126.09 | 15.41 |
| Example 7 | 4.0 | 0.028 (citric acid) | 80 | 123.67 | 10.43 |
| Example 8 | 3.0 | 0.09 (hydrochloric acid) | 79 | 106.95 | 5.29 |
| Comp. Ex. 1 | 4.0 | 0.15 | 114 | 264.73 | 40.18 |

Comp. Ex.: Comparative Example
SE: standard error

The results shown in Table 1 and FIG. 1 confirmed that the rocuronium preparation of the present invention significantly reduces vascular pain to be induced, and that a preparation having titratable acidity of about 40 mEq or less does not cause vascular pain.

INDUSTRIAL APPLICABILITY

The rocuronium preparation of the present invention significantly reduces vascular pain to be induced and is useful as a muscle relaxant under anesthesia.

The invention claimed is:

1. A rocuronium preparation consisting of rocuronium and a buffer solution and optionally one or more ingredients selected from the group consisting of a solvent, a solubilizing agent, a suspending agent, an isotonizing agent, a soothing agent, a preservative, an antioxidative agent, a stabilizing agent, and an antioxidant, wherein the preparation has a titratable acidity of 80 mEq or less and a pH of 2.5 to 4.5, with the proviso that the titratable acidity means the quantity (mEq) of sodium hydroxide consumed in titration of 1 L of a solution to pH 7.4.

2. The rocuronium preparation of claim 1, wherein the buffer solution is at least one selected from the group consisting of an acetate buffer solution, a citrate buffer solution, a formate buffer solution, a tartrate buffer solution, a phosphate buffer solution, a glycine-hydrochloric acid buffer solution, and a citric acid-phosphate buffer solution.

3. The rocuronium preparation of claim 1, which is an injection.

4. A method for producing the rocuronium preparation of claim 1, the method comprising a step of adjusting the titratable acidity of the rocuronium preparation consisting of rocuronium and a buffer solution and optionally one or more ingredients selected from the group consisting of a solvent, a solubilizing agent, a suspending agent, an isotonizing agent, a soothing agent, a preservative, an antioxidative agent, a stabilizing agent, and an antioxidant to 80 mEq or less and the pH of the preparation to 2.5 to 4.5.

5. A method for reducing and/or alleviating the vascular pain caused by a rocuronium preparation, the method comprising adjusting the titratable acidity of a rocuronium preparation consisting of rocuronium and a buffer solution and optionally one or more ingredients selected from the group consisting of a solvent, a solubilizing agent, a suspending agent, an isotonizing agent, a soothing agent, a preservative, an antioxidative agent, a stabilizing agent, and an antioxidant to 80 mEq or less and the pH of the preparation to 2.5 to 4.5, with the proviso that the titratable acidity means the quantity (mEq) of sodium hydroxide consumed in titration of 1 L of a solution to pH 7.4.

6. A method for producing the rocuronium preparation of claim 2, the method comprising a step of adjusting the titratable acidity of the rocuronium preparation consisting of rocuronium and a buffer solution and optionally one or more ingredients selected from the group consisting of a solvent, a solubilizing agent, a suspending agent, an isotonizing agent, a soothing agent, a preservative, an antioxidative agent, a stabilizing agent, and an antioxidant to 80 mEq or less and the pH of the preparation to 2.5 to 4.5.

7. A method for producing the rocuronium preparation of claim 3, the method comprising a step of adjusting the titratable acidity of the rocuronium preparation consisting of rocuronium and a buffer solution and optionally one or more ingredients selected from the group consisting of a solvent, a solubilizing agent, a suspending agent, an isotonizing agent, a soothing agent, a preservative, an antioxidative agent, a stabilizing agent, and an antioxidant to 80 mEq or less and the pH of the preparation to 2.5 to 4.5.

8. The rocuronium preparation of claim 1, wherein the buffer solution concentration is less than 0.1 M.

9. The rocuronium preparation of claim 1, wherein the buffer solution is at least one selected from the group consisting of a citrate buffer solution, a formate buffer solution, a tartrate buffer solution, a phosphate buffer solution, a glycine-hydrochloric acid buffer solution, and a citric acid-phosphate buffer solution.

10. The rocuronium preparation of claim 1, consisting of rocuronium, a buffer solution and a isotonizing agent, and optionally one or more ingredients selected from the group consisting of a solvent, a solubilizing agent, a suspending agent, a soothing agent, a preservative, an antioxidative agent, a stabilizing agent, and an antioxidant.

\* \* \* \* \*